(12) United States Patent
Lupold et al.

(10) Patent No.: US 6,933,114 B2
(45) Date of Patent: Aug. 23, 2005

(54) NUCLEIC ACID LIGANDS TO THE PROSTATE SPECIFIC MEMBRANE ANTIGEN

(75) Inventors: Shawn E. Lupold, Alexandria, VA (US); Yun Lin, Louisville, CO (US); Brian J. Hicke, Boulder, CO (US); Donald S. Coffey, Lutherville, MD (US)

(73) Assignee: Gilead Sciences, Inc., Foster City, CA (US)

( * ) Notice: Subject to any disclaimer, the term of this patent is extended or adjusted under 35 U.S.C. 154(b) by 515 days.

(21) Appl. No.: 09/978,969

(22) Filed: Oct. 16, 2001

(65) Prior Publication Data

US 2002/0119473 A1 Aug. 29, 2002

Related U.S. Application Data

(60) Provisional application No. 60/278,830, filed on Mar. 26, 2001, and provisional application No. 60/240,781, filed on Oct. 16, 2000.

(51) Int. Cl.⁷ .......................... C12Q 1/68; C07H 21/04; C12N 14/00
(52) U.S. Cl. .......................... 435/6; 435/91.2; 530/344; 530/350; 536/23.1; 536/25.4
(58) Field of Search .................... 435/6, 91.2; 530/344, 530/350; 536/23.1, 25.4

(56) References Cited

U.S. PATENT DOCUMENTS

| | | | |
|---|---|---|---|
| 5,270,163 A | | 12/1993 | Gold et al. |
| 5,538,866 A | | 7/1996 | Israeli et al. |
| 5,582,981 A | * | 12/1996 | Toole et al. .................... 435/6 |
| 5,723,323 A | | 3/1998 | Kauffman et al. |
| 5,886,155 A | * | 3/1999 | Armah et al. ................ 530/395 |
| 5,928,871 A | * | 7/1999 | Heintz et al. ................... 435/6 |
| 6,020,483 A | * | 2/2000 | Beckervermit et al. .. 536/27.11 |
| 6,287,765 B1 | * | 9/2001 | Cubicciotti .................... 435/6 |

FOREIGN PATENT DOCUMENTS

| | | |
|---|---|---|
| GB | 2 183 661 A | 6/1987 |
| WO | WO89/06694 | 7/1989 |
| WO | WO 91/19813 | 12/1991 |
| WO | WO92/14843 | 9/1992 |

OTHER PUBLICATIONS

Chang et al. (Oct. 1999) Clin. Cancer Res. 5:2674–2681.
Joyce (1989) Gene 82:83–87.
Joyce & Inoue (1989) Nucleic Acids Research 17:711–722.
Ellington & Szostak (May 1990) Abstracts of papers presented at the 1990 meeting on RNA Processing, Cold Spring Harbor Laboratory, Cold Spring Harbor, NY, p. 84.
Kinzler & Vogelstein (1989) Nucleic Acids Research 17:3645–3653.
Kramer et al. (1974) J. Mol. Biol. 89:719–736.
Levisohn & Spiegelman (1969) Proc. Natl. Acad. Sci. USA 63:805–811.
Levisohn & Spiegelman (1968) Proc. Natl. Acad. Sci. USA 60:866–872.
Liu et al. (Sep. 1997) Cancer Res. 57:3629–3634.
Lopes et al. (Oct. 1990) Cancer Res. 50:6423–6429.
McDevitt et al. (Nov. 2000) Cancer Res. 60:6095–6100.
Murphy et al. (1999) The Prostate 39:54–59.
Oliphant et al. (Jul. 1989) Mol. Cell. Biol. 9:2944–2949.
Oliphant & Struhl (1988) Nucleic Acids Research 16:7673–7683.
Oliphant & Struhl (1987) Methods in Enzymology 155:568–583.
Oliphant et al. (1986) Gene 44:177–183.
Robertson & Joyce (Mar. 1990) Nature 344:467–468.
Sodee et al. (1998) The Prostate 37:140–148.
Szostak, (1988) "Structure and Activity of Ribozymes," in *Redesigning the Molecules of Life*, (S.A. Benner ed.) Springer–Verlag Berline Heidelberg, pp. 87–113.
Thiesen & Bach (1990) Nucleic Acids Research 18:3203–3208.

* cited by examiner

*Primary Examiner*—B J Forman
(74) *Attorney, Agent, or Firm*—Swanson & Bratschun, LLC

(57) ABSTRACT

Methods are provided for generating nucleic acid ligands of Prostate Specific Membrane Antigen (PSMA). The methods of the invention use the SELEX method for the isolation of nucleic acid ligands. The invention also includes nucleic acid ligands to PSMA, and methods and compositions for the treatment and diagnosis of disease using the nucleic acid ligands.

1 Claim, 11 Drawing Sheets

| | | |
|---|---|---|
| 40N7 Library | GGGAGGACGAUGCGGNNNNNNNNNNNNNNNNNNNNNNNNNNNNNNNNNNNNNNNNCAGACGACUCGCCCGA | |
| xPSM-A9 | GGGAGGACGAUGCGGACCGAAAAGACCUGACUUCUAUACUAAGUCUACGUUCCAGACGACUCGCCCGA | 55% |
| xPSM-A10 | GGGAGGACGAUGCGGAUCAGCCAUGUUUACGUCACUCCCUGUCAAUCCUCAUCGGCAGACGACUCGCCCGA | 40% |

Fig. 6

NUCLEIC ACID LIGANDS TO THE PROSTATE SPECIFIC MEMBRANE ANTIGEN

CROSS-REFERENCE TO RELATED APPLICATIONS

This application claims the benefit of United States Provisional Patent Application No. 60/278,830, filed Mar. 26, 2001, entitled "Nucleic Acid Ligands to the Prostate Specific Membrane Antigen". This application also claims the benefit of United States Provisional Patent Application No. 60/240, 781, filed Oct. 16, 2000, entitled "Nucleic Acid Ligands to the Prostate Specific Membrane Antigen"

FIELD OF THE INVENTION

Described herein are high affinity nucleic acid ligands to Prostate Specific Membrane Antigen (PSMA). Also described herein are methods for identifying and preparing high affinity nucleic acid ligands to PSMA. The method used herein for identifying such nucleic acid ligands is called SELEX, an acronym for Systematic Evolution of Ligands by Exponential enrichment. Further disclosed are RNA ligands to PSMA. Also included are oligonucleotides containing nucleotide derivatives chemically modified at the 2' positions of pyrimidines. Additionally disclosed are RNA ligands to PSMA containing 2'-F modifications. The invention also includes high affinity nucleic acid ligand inhibitors of PSMA. The oligonucleotides of the present invention are useful as diagnostic agents and/or therapeutic agents.

BACKGROUND OF THE INVENTION

The Prostate Specific Membrane Antigen (PSMA) is a 750-amino acid type II transmembrane protein. PSMA is expressed by prostatic epithelial cells and extraprostatic expression has been detected in the brain, kidney, salivary gland and duodenum. (See e.g. Renneberg et al. (1999) Urol. Res. 27(1):23–7; Troyer et al. (1995) Int. J. Cancer 62(5): 552–8; Israel et al. (1994) Cancer Res. 54(7):1807–11; Israel et al. (1993) Cancer Res. 53(2):227–30). PSMA is a carboxypeptidase which cleaves N-acetyl-asp-glu. PSMA has three domains: a 19-amino acid cytoplasmic domain, a 24-amino acid transmembrane domain, and a 707-amino acid extracellular domain. A monoclonal antibody specific to the cytoplasmic domain, 7E11.C5, has been adapted for in vivo imaging of prostatic cancer through radiolabeling with indium-111. (Elgamal et al. (1998) Prostate 37(4):261–9; Lamb and Faulds (1998) Drugs Aging 12(4):293–304).

Since its discovery in 1987 (Horoszewicz et al. (1987) Anticancer Res. 7:927–35), PSMA has been considered an excellent prostate tumor cell marker. PSMA expression is primarily prostate specific, with barely detectable levels seen in the brain, salivary glands, and small intestine (Israeli et al. (1994) Cancer Res. 54:1807–11). Additionally, PSMA expression is high in malignant prostate cells, with the highest expression in androgen resistant cells due to negative regulation by androgens (Wright et al. (1996) Urology 48:326–34). Furthermore, PSMA is alternatively spliced, where normal prostate cells predominantly express a cytosolic form named PSM' and malignant cells express the characteristic full-length membrane bound form (Su et al. (1995) Cancer Res. 55:1441–3). This full-length PSMA is a type II membrane glycoprotein, in which the majority of the protein is extracellular and available as a target for diagnostic and therapeutic agents. These properties have made PSMA an ideal target for prostate cancer immunotherapy (Murphy et al. (1999) Prostate 39:54–9); monoclonal antibody imaging (Sodee et al. (1998) Prostate 37:140–8); and therapy (McDevitt et al. (2000) Cancer Res. 60:6095–100). The first anti-PSMA antibody was quickly modified into an imaging agent (Lopes et al. (1990) Cancer Res. 50:6423–6429), which is currently used clinically to diagnose metastatic prostate tumors. Additionally, PSMA is expressed by neovascular endothelial cells in a variety of cancers (Chang et al. (1999) Clin. Cancer Res. 5:2674–81; Liu et al. (1997) Cancer Res. 57:3629–34), making it a candidate target for tumor vascular imaging and anti-angiogenesis therapy.

An aptamer that recognizes PSMA's extracellular domain has potential utility as a therapeutic entity, via inhibition of PSMA enzymatic activity, as an in vivo imaging agent, and additionally as a targeting agent for therapeutic delivery of cytotoxic chemicals and radionuclides. The use of proteins as drugs and reagents is often limited by the activity of proteases, the size of the protein, transport and the ability of an organism to make antibodies against that protein. Many of these limitations can be circumvented by the use of aptamers, made of synthesized RNA, that are stabilized against nuclease activity. Relative to antibodies, aptamers are small (7–20 kDa), clear very rapidly from blood, and are chemically synthesized. Rapid blood clearance is important for in vivo diagnostic imaging, where blood levels are a primary determinant of background that obscures an image. Rapid blood clearance may also be important in therapy, where blood levels may contribute to toxicity. SELEX technology allows rapid aptamer isolation, and chemical synthesis enables facile and site-specific conjugation of aptamers to a variety of inert and bioactive molecules. An aptamer to PSMA would therefore be useful for tumor therapy or in vivo or ex vivo diagnostic imaging and/or for delivering a variety of therapeutic agents complexed with the PSMA nucleic acid ligand for treatment of disease conditions in which PSMA is expressed.

The development of the Systematic Evolution of Ligands by Exponential Enrichment (SELEX) process has provided a new alternative, nuclease-resistant oligonucleotides that can be selected to bind tightly and specifically to almost any ligand. (Tuerk and Gold (1990) Science 249:505–10; Ellington and Szostak (1990) Nature 346:818–22; Lin et al. (1994) Nucleic Acids Res. 22:5229–34; Gold (1995) J. Biol. Chem. 270:13581–4); for example: organic dyes, antibiotics, amino acids, and cells (Ellington and Szostak (1990) Nature 346:818–22; Wang and Rando (1995) Chem. Biol. 2:281–90; Connell et al. (1993) Biochemistry 32:5497–502; Morris et al. (1998) Proc. Natl Acad. Sci. USA 95:2902–7). These synthetic oligonucleotide sequences, termed "RNA aptamers," have been made to bind over 100 target ligands and are emerging as a new class of molecules that contest antibodies in therapeutics, imaging, and diagnostics (Hicke and Stephens (2000) J. Clin. Invest. 106:923–8; Jayasena (1999) Clin. Chem. 45:1628–50).

The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096, entitled "Nucleic Acid Ligands," and U.S. Pat. No. 5,270,163 (see also WO 91/19813), entitled "Methods for Identifying Nucleic Acid Ligands," each of which is specifically incorporated herein by reference in its entirety. Each of these applications, collectively referred to herein as the SELEX Patent Applications, describes a fundamentally novel method for making a nucleic acid ligand to any desired target molecule.

The SELEX process provides a class of products which are referred to as nucleic acid ligands or aptamers, each having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. Nos. 5,763,177 and 6,011,577, both entitled "Systematic Evolution of Ligands by Exponential Enrichment: Photoselection of Nucleic Acid Ligands and Solution SELEX," describe a SELEX based method for selecting nucleic acid ligands containing photoreactive groups capable of binding and/or photocrosslinking to and/or photoinactivating a target molecule. U.S. Pat. No. 5,580,737, entitled "High-Affinity Nucleic Acid Ligands That Discriminate Between Theophylline and Caffeine," describes a method for identifying highly specific nucleic acid ligands able to discriminate between closely related molecules, which can be non-peptide, termed Counter-SELEX. U.S. Pat. No. 5,567,588, entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985, entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2' modified pyrimidines.

The SELEX method encompasses combining selected oligonucleotides with other selected oligonucleotides and non-oligonucleotide functional units as described in U.S. Pat. No. 5,637,459, entitled "Systematic Evolution of Ligands by EXponential Enrichment: Chimeric SELEX," and U.S. Pat. No. 5,683,867, entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. Pat. No. 6,011,020, entitled "Nucleic Acid Ligand Complexes." Each of the above described patent applications which describe modifications of the basic SELEX procedure are specifically incorporated by reference herein in their entirety.

Since the first discovery of RNA aptamers as ligand binding agents (Tuerk and Gold (1990) Science 249:505–10; Ellington and Szostak (1990) Nature 346:818–22), an enormous diversity of target molecules have been identified (Famulok et al. (2000) Acc. Chem. Res. 33:591–9). The diversity of structures employed by an aptamer library allows tight binding RNA ligands from targets as simple as a single amino acid (Connell et al. (1993) Biochemistry 32:5497–502), to complex targets such as red blood cells (Morris et al. (1998) Proc. Natl Acad. Sci. USA 95:2902–7). Despite the success of this technique, however, there are no reported RNA aptamers to membrane bound tumor antigens. Therefore, the possibility of identifying and producing nuclease stable RNA aptamers that bind to and inhibit the enzymatic activity of the well-known prostate tumor cell surface antigen, PSMA was explored.

It is an object of the present invention to provide methods that can be used to identify nucleic acid ligands that bind with high specificity and affinity to PSMA.

It is a further object of the present invention to obtain nucleic acid ligands to PSMA that inhibit the activity of PSMA when bound.

It is a further object of the present invention to provide a complex for use in in vivo or ex vivo diagnostics comprising one or more PSMA nucleic acid ligands and one or more markers.

It is a further object of this invention to provide a method for delivering therapeutic agents for the treatment or prophylaxis of disease conditions in which PSMA is expressed.

SUMMARY OF THE INVENTION

The present invention includes methods for identifying and producing nucleic acid ligands to the Prostate Specific Membrane Antigen (PSMA) and the nucleic acid ligands so identified and produced. The method uses the SELEX process for the Systematic Evolution of Ligands by EXponential enrichment. In particular, novel nuclease resistant RNA sequences are provided which are capable of binding specifically to the extracellular portion of PSMA using a Baculovirus-purified PSMA fusion protein as the target protein. The method described herein is the first application of SELEX to a membrane tumor antigen. Also included are oligonucleotides containing nucleotide derivatives modified at the 2' position of the pyrimidines. Specifically included in the invention are the RNA ligand sequences shown in Table 3 (SEQ ID NOS:3–27). The high affinity to PSMA of two of these unique aptamer sequences, xPSM-A9 and xPSM-A10 (SEQ ID NOS:5 & 15), was demonstrated by their ability to inhibit native PSMA N-acetyl-alpha-linked-acid dipeptidase (NAALADase) activity. These aptamers bind to the extracellular portion of PSMA and inhibit native PSMA enzymatic activity with low nanomolar $K_I$'s. The nucleic acid ligands of the invention can be used clinically to inhibit PSMA enzymatic activity or can be modified to carry agents for imaging or delivery of therapeutic agents to prostate cancer cells.

BRIEF DESCRIPTION OF THE FIGURES

As illustrated in FIG. 5 in vitro selection rounds inhibit NAALADase activity, whereas the initial pool shows no inhibition. Round six of xPSM binding selection shows the best IC50 when compared to both early and late round selections. The original random RNA has no effect on NAALADase activity in these ranges. (○) Random RNA; (■) Round 3; (▲) Round 6; (♦) Round 8; (*) Round 9.

FIG. 6 depicts the 40N7 Library which is the complement to SEQ ID NO: 1 and individual aptamer sequences from round 6. The original diversity of ~$10^{14}$ RNA sequences was selected to essentially two aptamer sequences, xPSM-A9 (SEQ ID NO:5 and xPSM-A10 (SEQ ID NO:15).

In FIG. 7A, 30 nM of aptamer xPSM-A10 shows competitive inhibition, with a calculated $K_I$ of 11.9 nM. Alternatively, in FIG. 7B, 1 nM of aptamer xPSM-A9 shows noncompetitive inhibition, with a calculated $K_I$ of 1.1 nM. In both graphs: (■) is xPSM and (○) is xPSM plus aptamer inhibitor. $R^2$ values A:xPSM 0.7932, A:xPSM-A10 0.887, B:xPSM 0.8155, B:xPSM-A9 0.7248.

DETAILED DESCRIPTION OF THE INVENTION

Figure 1:
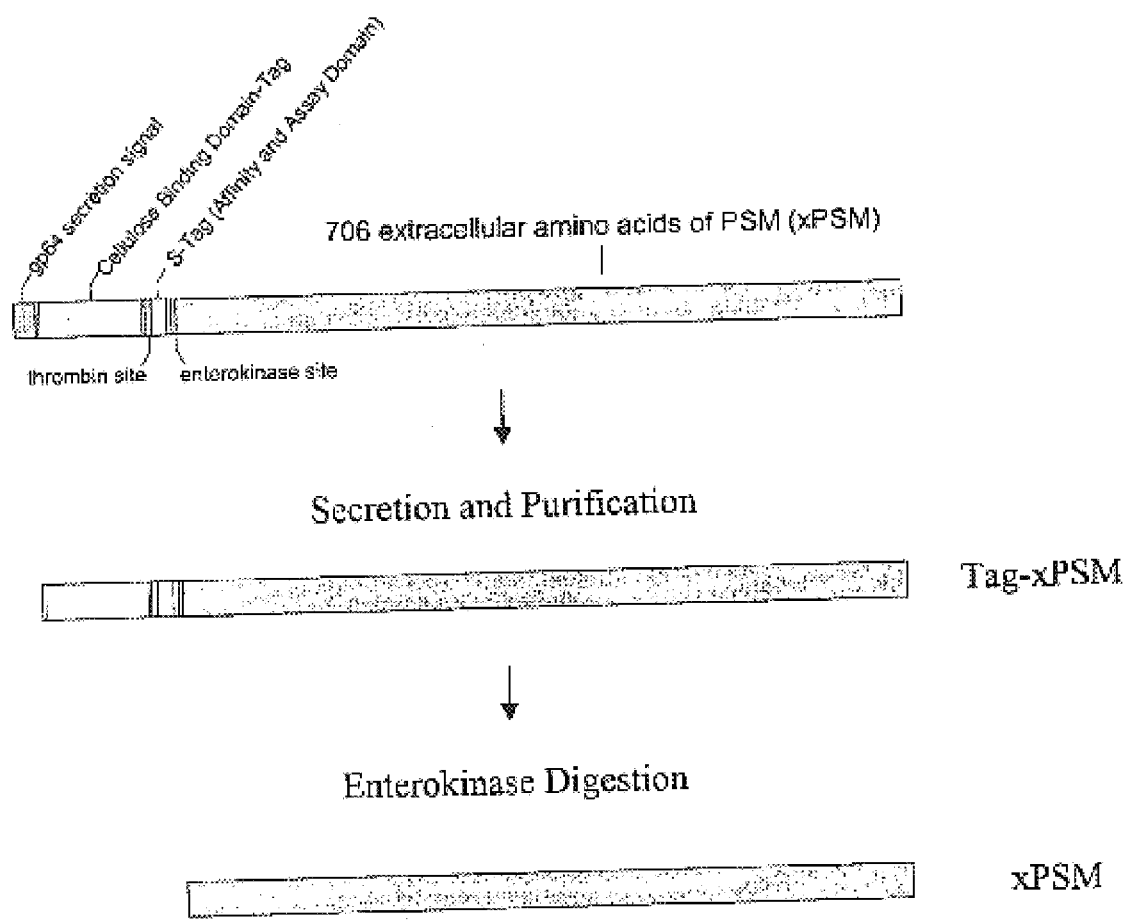
FIG. 1 illustrates the design of in vitro selection target, the extracellular portion of PSMA. Recombinant baculovirus expressing the fusion protein secrete Tag-xPSM via the gp64 secretion signal. This fusion protein is purified from the media using a cellulose column or S-protein agarose beads. A protein coding for only the extracellular portion of PSMA (xPSM) is released by enterokinase cleavage.

The central method utilized herein for identifying nucleic acid ligands to PSMA is called the SELEX process, an acronym for Systematic Evolution of Ligands by Exponential enrichment. The SELEX method involves: (a) contacting the candidate mixture of nucleic acids with PSMA, or expressed domains or peptides corresponding to PSMA; (b) partitioning between members of said candidate mixture on the basis of affinity to PSMA; and (c) amplifying the selected molecules to yield a mixture of nucleic acids enriched for nucleic acid sequences with a relatively higher affinity for binding to PSMA.

The invention includes RNA ligands to PSMA. This invention further includes the specific RNA ligands to PSMA shown in Table 3 (SEQ ID NOS:3–27). More specifically, this invention includes nucleic acid sequences that arc substantially homologous to and that have substantially the same ability to bind PSMA as the specific nucleic acid ligands shown in Table 3. By substantially homologous it is meant a degree of primary sequence homology in excess of 70%, most preferably in excess of 80%, and even more preferably in excess of 90%, 95%, or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. Substantially the same ability to bind PSMA means that the affinity is within one or two orders of magnitude of the affinity of the ligands described herein. It is well within the skill of those of ordinary skill in the art to determine whether a given sequence—substantially homologous to those specifically described herein—has the same ability to bind PSMA.

A review of the sequence homologies of the nucleic acid ligands of PSMA shown in Table 3 shows that sequences with little or no primary homology may have substantially the same ability to bind PSMA. For this reason, this invention also includes nucleic acid ligands that have substantially the same postulated structure or structural motifs and ability to bind PSMA as the nucleic acid ligands shown in Table 3. Substantially the same structure or structural motifs can be postulated by sequence alignment using the Zukerfold program (see Zuker (1989) Science 244:48–52). As would be known in the art, other computer programs can be used for predicting secondary structure and structural motifs. Substantially the same structure or structural motif of nucleic acid ligands in solution or as a bound structure can also be postulated using NMR or other techniques as would be known in the art.

Also included in this invention is a method for detecting the presence of a disease that is expressing PSMA in a biological tissue which may contain the disease by the method of: (a) identifying a nucleic acid ligand from a candidate mixture of nucleic acids, the nucleic acid ligand being a ligand of PSMA, by the method comprising (i) contacting a candidate mixture of nucleic acids with PSMA, wherein nucleic acids having an increased affinity to PSMA relative to the candidate mixture may be partitioned from the remainder of the candidate mixture; (ii) partitioning the increased affinity nucleic acids from the remainder of the candidate mixture; (iii) amplifying the increased affinity nucleic acids to yield a mixture of nucleic acids with relatively higher affinity and specificity for binding to PSMA, whereby a nucleic acid ligand of PSMA is identified; (b) attaching a marker that can be used in in vivo or ex vivo diagnostics to the nucleic acid ligand identified in step (iii) to form a marker-nucleic acid ligand complex; (c) exposing a tissue which may contain the disease to the marker-nucleic acid ligand complex; and (d) detecting the presence of the marker-nucleic acid ligand in the tissue, whereby a disease expressing PSMA is identified.

Further included in this invention is a complex for use in in vivo or ex vivo diagnostics comprising one or more PSMA nucleic acid ligands and one or more markers. Still further included in this invention is a method for delivering therapeutic agents for the treatment or prophylaxis of disease conditions in which PSMA is expressed.

Definitions

Various terms are used herein to refer to aspects of the present invention. To aid in the clarification of the description of the components of this invention, the following definitions are provided.

As used herein a "nucleic acid ligand" is a non-naturally occurring nucleic acid having a desirable action on a target. Nucleic acid ligands are often referred to as "aptamers." A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In a preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand does not have the known physiological function of being bound by the target molecule. In the present invention, the target is PSMA, or regions thereof. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein a "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2' position sugar modifications, 5 position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands that interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to PSMA.

The SELEX methodology is described in the SELEX Patent Applications.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX target is PSMA. In particular, the SELEX targets in this application include purified PSMA, and fragments thereof, and short peptides or expressed protein domains comprising PSMA.

As used herein, "solid support" is defined as any surface to which molecules may be attached through either covalent or non-covalent bonds. This includes, but is not limited to, membranes, microtiter plates, magnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces.

"Complex" as used herein means the molecular entity formed by the covalent linking of one or more PSMA nucleic acid ligands with one or more markers. In certain embodiments of the present invention, the complex is depicted as A-B-Y, wherein A is a marker; B is optional, and comprises a linker; and Y is a PSMA nucleic acid ligand.

"Marker" as used herein is a molecular entity or entities that when complexed with the PSMA nucleic acid ligand, either directly or through a linker(s) or spacer(s), allows the detection of the complex in an in vivo or ex vivo setting through visual or chemical means. Examples of markers include, but are not limited to radionuclides, including Tc-99m, Re-188, Cu-64, Cu-67, F-18, $^{125}$I, $^{131}$I, $^{32}$P, $^{186}$Re; $^{111}$In; all fluorophores, including fluorescein, rhodamine, Texas Red; derivatives of the above fluorophores, including Rhodamine-Red-X; magnetic compounds; and biotin.

As used herein, "linker" is a molecular entity that connects two or more molecular entities through covalent bond or non-covalent interactions, and can allow spatial separation of the molecular entities in a manner that preserves the functional properties of one or more of the molecular entities. A linker can also be known as a spacer. Examples of a linker include, but are not limited to, the $(CH_2CH_2O)_6$ and hexylamine structures shown in FIG. 2 of U.S. patent application Ser. No. 09/364,902, filed Jul. 29, 1999, entitled "Tenascin-C Nucleic Acid Ligands," which is incorporated herein by reference in its entirety.

"Therapeutic" as used herein, includes treatment and/or prophylaxis. When used, therapeutic refers to humans, as well as, other animals.

"Covalent Bond" is the chemical bond formed by the sharing of electrons.

"Non-covalent Interactions" are means by which molecular entities are held together by interactions other than Covalent Bonds including ionic interactions and hydrogen bonds.

As used herein "PSMA" refers to purified protein, the extracellular, including xPSM, cytoplasmic, or intracellular domains of the protein or any allelic variants thereof. "PSMA" as used herein also includes the protein isolated from a species other than humans.

Note, that throughout this application various citations are provided. Each citation is specifically incorporated herein in its entirety by reference.

In the preferred embodiment, the nucleic acid ligands of the present invention are derived from the SELEX methodology. The SELEX process is described in U.S. patent application Ser. No. 07/536,428, entitled "Systematic Evolution of Ligands by Exponential Enrichment," now abandoned, U.S. Pat. No. 5,475,096, entitled "Nucleic Acid Ligands," and U.S. Pat. No. 5,270,163 (see also WO 91/19813), entitled "Methods for Identifying Nucleic Acid Ligands." These applications, each specifically incorporated herein by reference, are collectively called the SELEX Patent Applications.

The SELEX process provides a class of products that are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

In its most basic form, the SELEX process may be defined by the following series of steps.

1. A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below; (b) to mimic a sequence known to bind to the target; or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2. The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3. The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4. Those nucleic acids selected during partitioning as having the relatively higher affinity for the target are then amplified to create a new candidate mixture that is enriched in nucleic acids having a relatively higher affinity for the target.

5. By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. Nos. 5,763,177 and 6,001,577, both entitled "Systematic Evolution of Ligands by Exponential Enrichment: Photoselection of Nucleic Acid Ligands and Solution SELEX," all describe a SELEX based method for selecting nucleic acid ligands containing photoreactive groups capable of binding and/or photocrosslinking to and/or photoinactivating a target molecule. U.S. Pat. No. 5,580,737, entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588, entitled "Systematic Evolution of Ligands by Exponential Enrichment: Solution SELEX," describes a SELEX-based method which achieves highly efficient partitioning between oligonucleotides having high and low affinity for a target molecule. U.S. Pat. No. 5,496,938, entitled "Nucleic Acid Ligands to HIV-RT and HIV-1 Rev," describes methods for obtaining improved nucleic acid ligands after SELEX has been performed. U.S. Pat. No. 5,705,337, entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985, entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459, entitled "Systematic Evolution of Ligands by Exponential Enrichment: Chimeric SELEX," and U.S. Pat. No. 5,683,867, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

In U.S. Pat. No. 5,496,938, methods are described for obtaining improved nucleic acid ligands after the SELEX process has been performed. This patent, entitled "Nucleic Acid Ligands to HIV-RT and HIV-1 Rev," is specifically incorporated herein by reference.

One potential problem encountered in the diagnostic use of nucleic acids is that oligonucleotides in their phosphodiester form may be quickly degraded in body fluids by intracellular and extracellular enzymes, such as endonucleases and exonucleases, before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 8, 1993, now abandoned and U.S. Pat. No. 5,660,985, both entitled "High Affinity Nucleic Acid Ligands Containing Modified Nucleotides," and U.S. patent application Ser. No. 09/362,578, filed Jul. 28, 1999, entitled "Transcription-free SELEX," each of which is specifically incorporated herein by reference in its entirety. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases, isocytidine and isoguanidine and the like. Modifications can also include 3' and 5' modifications such as capping. In preferred embodiments of the instant invention, the nucleic acid ligands are RNA molecules that are 2'-fluoro (2'-F) modified on the sugar moiety of pyrimidine residues.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

The nucleic acid ligands of the invention are prepared through the SELEX methodology that is outlined above and thoroughly enabled in the SELEX applications incorporated herein by reference in their entirety.

In preferred embodiments, the SELEX process is carried out using fragments of PSMA that are bound to magnetic beads through hydrophobic interactions. A candidate mixture of single stranded RNA molecules is then contacted with the magnetic beads in a microfuge tube. After incubation for a predetermined time at a selected temperature, the beads are held to the sides of the tube by a magnetic field, and the microfuge tube is washed to remove unbound candidate nucleic acid ligands. The nucleic acid ligands that bind to the PSMA are then released into solution in the microfuge tube, then reverse transcribed by reverse transcriptase and amplified using the Polymerase Chain Reaction (PCR). The amplified candidate mixture is then used to begin the next round of the SELEX process.

In certain embodiments of the present invention, the nucleic acid ligands to PSMA described herein are useful for diagnostic purposes and can be used to image pathological conditions (such as human tumor imaging). In addition to diagnosis, the PSMA nucleic acid ligands are useful in the prognosis and monitoring of disease conditions in which PSMA is expressed.

Diagnostic agents need only be able to allow the user to identify the presence of a given target at a particular locale or concentration. Simply the ability to form binding pairs with the target may be sufficient to trigger a positive signal for diagnostic purposes. Those skilled in the art would be able to adapt any PSMA nucleic acid ligand by procedures known in the art to incorporate a marker in order to track the presence of the nucleic acid ligand. Such a marker could he used in a number of diagnostic procedures, such as detection of primary and metastatic tumors. In one embodiment the labeling marker is technetium-99 m; however, other markers such as additional radionuclides, magnetic compounds, fluorophores, biotin, and the like can be conjugated to the PSMA nucleic acid ligand for imaging in an in vivo or ex vivo setting disease conditions in which PSMA is expressed. The marker may be covalently bound to a variety of positions on the PSMA nucleic acid ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the PSMA nucleic acid ligand. In embodiments where the marker is technetium-99 m, preferably it is bonded to the 5' or 3' hydroxyl of the phosphate group thereof or to the 5 position of a modified pyrimidine. In the most preferred embodiment, the marker is bonded to the 5' hydroxyl of the phosphate group of the nucleic acid ligand with or without a linker. In another embodiment, the marker is conjugated to the nucleic acid ligand by incorporating a pyrimidine containing a primary amine at the 5 position, and use of the amine for conjugation to the marker. Attachment of the marker can be done directly or with the utilization of a linker. In the embodiment where technetium-99 m is used as the marker, the preferred linker is a hexylamine linker.

In other embodiments, the PSMA nucleic acid ligands are useful for the delivery of therapeutic compounds (including, but not limited to, cytotoxic compounds, immune enhancing substances and therapeutic radionuclides) to tissues or organs expressing PSMA. Disease conditions in which PSMA may be expressed include cancer. Those skilled in the art would be able to adapt any PSMA nucleic acid ligand by procedures known in the art to incorporate a therapeutic compound in a complex. The therapeutic compound may be covalently bound to a variety of positions on the PSMA nucleic acid ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the PSMA nucleic acid ligand. In the preferred embodiment, the therapeutic agent is bonded to the 5' amine of the nucleic acid ligand. Attachment of the therapeutic agent can be done directly or with the utilization of a linker. In embodiments in which cancer is the targeted disease, 5-fluorodeoxyuracil or other nucleotide analogs known to be active against tumors can be incorporated internally into existing U's within the PSMA nucleic acid ligand or can be added internally or conjugated to either terminus either directly or through a linker. In addition, both pyrimidine analogues 2',2'-difluorocytidine and purine analogues (deoxycoformycin) can be incorporated. In addition, U.S. application Ser. No. 08/993,765, filed Dec. 18, 1997, entitled "Nucleotide Based Prodrugs," incorporated herein by reference in its entirety, describes, inter alia, nucleotide-based prodrugs comprising nucleic acid ligands directed to tumor cells for precisely localizing chemoradiosensitizers, and radiosensitizers and radionuclides and other radiotherapeutic agents to the tumor.

It is also contemplated that both the marker and therapeutic agent may be associated with the PSMA nucleic acid ligand such that detection of the disease condition and delivery of the therapeutic agent is accomplished together in one aptamer or as a mixture of two or more different modified versions of the same aptamer. It is also contemplated that either or both the marker and/or the therapeutic agent may be associated with a non-immunogenic, high molecular weight compound or lipophilic compound, such as a liposome. Methods for conjugating nucleic acid ligands with lipophilic compounds or non-immunogenic compounds in a diagnostic or therapeutic complex are described in U.S. Pat. No. 6,011,020, filed May 4, 1995, entitled "Nucleic Acid Ligand Complexes," which is incorporated herein in its entirety.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following examples are provided to explain and illustrate the present invention and are not to be taken as limiting of the invention.

Example 1 describes the materials and experimental procedures used for the generation of RNA ligands to PSMA. Purified PSMA protein was required for the in vitro selection of aptamers. Because the ultimate application of these aptamers is to bind prostate cancer cells in vivo, only the extracellular portion of PSMA was considered a sufficient target. A vector was therefore designed to express only the extracellular portion of PSMA, with removable affinity tags.

A baculovirus expression vector encoding only the extracellular portion of PSMA, termed xPSM was designed as described in Example 1 and illustrated schematically in FIG. 1. With reference to FIG. 1, a fragment of PSMA cDNA, coding only for the 706 extracellular amino acids of full length PSMA, was cloned into the multiple cloning site of the baculoviral transfer vector, pBACgus-10. This vector was designed to provide high levels fusion protein in the growth medium, which can be purified by affinity tags and released by enterokinase cleavage. The resulting transfer plasmid, pBACgus-PSM, was sequenced to confirm correct coding frame and sequence integrity. Both pBACgus-PSM and BACvector3000 linear DNA were co-transfected into Sf-9 cells and resulting recombinant viral plaques were purified and screened for expression of Tag-xPSM. A single recombinant baculovirus was then used for large-scale infections under serum free conditions.

Figure 2:
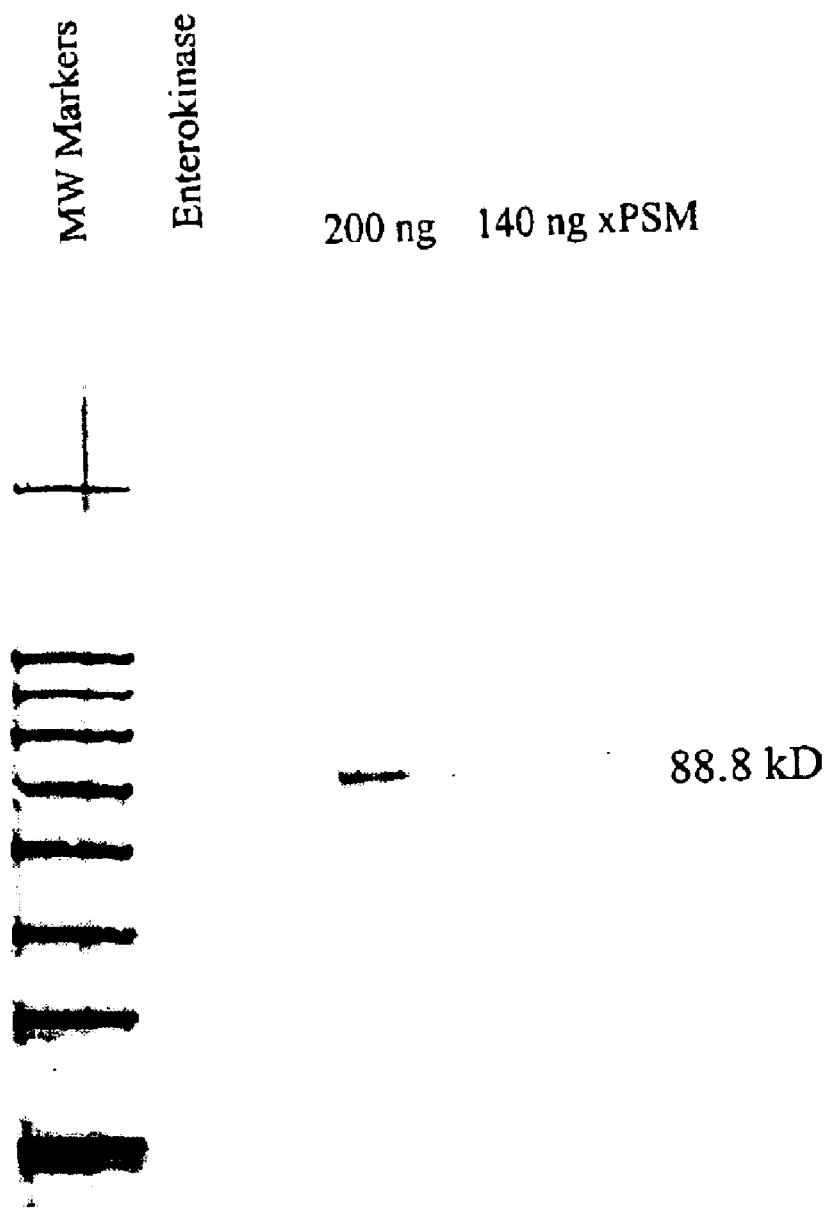
FIG. 2 depicts a silver stain of the purified xPSM protein. The purity of xPSM is evident by silver staining. The negative control shows that no protein is released in the absence of enterokinase. The size of purified xPSM has been calculated as approximately 90 kD, suggesting glycosylation of the expected 79.5 kD product.

Infected cell media was harvested 72–80 hours post infection and incubated with S-protein agarose to capture Tag xPSM. A recombinant enterokinase was then used to free xPSM. Following digestion, the enterokinase was captured with affinity resin, leaving only pure xPSM in the supernatant. The purity of the protein was determined by silver staining, with no Tag-xPSM evident by minus enterokinase control (FIG. 2). The size of purified xPSM has been calculated as ~90 kD, suggesting glycosylation of the expected 79.5 kD product.

Figure 3:
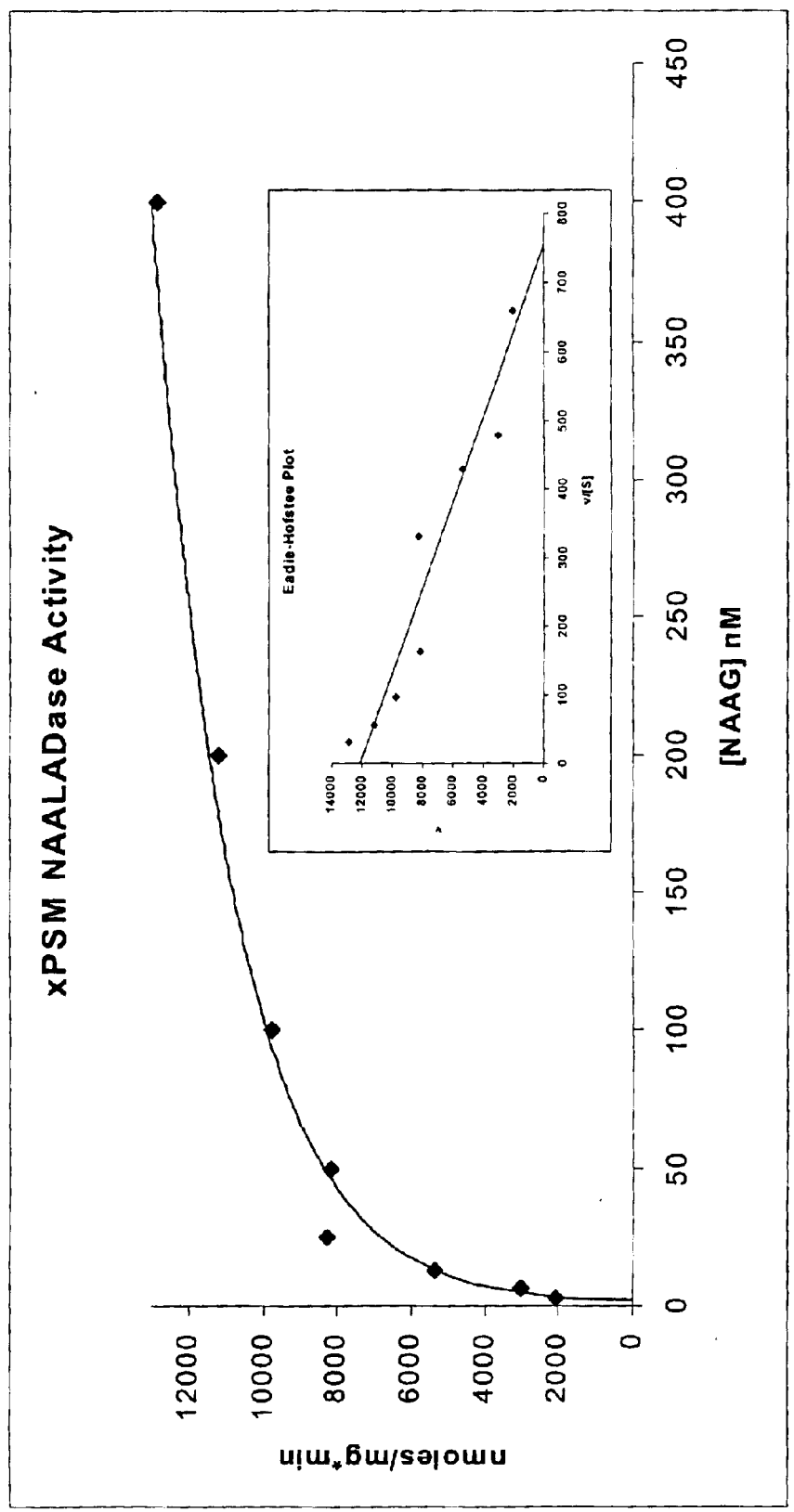
FIG. 3 depicts the NAALADase activity of the xPSM fusion protein. Purified xPSM displays native NAALADase activity with a $K_m$ of 16.1 nM and $V_{max}$ of 13 mmoles/mg*min.

The xPSM fusion protein was then tested for enzymatic activity to ensure native protein conformation. This is important to avoid evolving aptamers that recognize an improperly folded-fusion protein, but not the native enzyme. The purified xPSM protein showed expected NAALADase activity, with a $K_m$ of 16.1 nM and a $V_{max}$ of 13 mmoles/mg*min as illustrated in FIG. 3. The purified protein was immobilized on magnetic beads as a means to partition bound RNA aptamers during selection. A fraction of the xPSM remained NAALADase active while bound to the beads.

The in vitro selection strategy was designed to identify aptamers that would be applicable under physiologic conditions. To ensure nuclease stability, 2'-F modified pyrimidines were used in all transcriptions. Fluoropyrimidine RNA aptamers have been reported to be stable in serum for several hours. (Lin et al. (1994) Nucleic Acids Res. 22:5229–34). Additionally, aptamers were allowed to bind target only at 37° C., pH 7.4.

Figure 4:
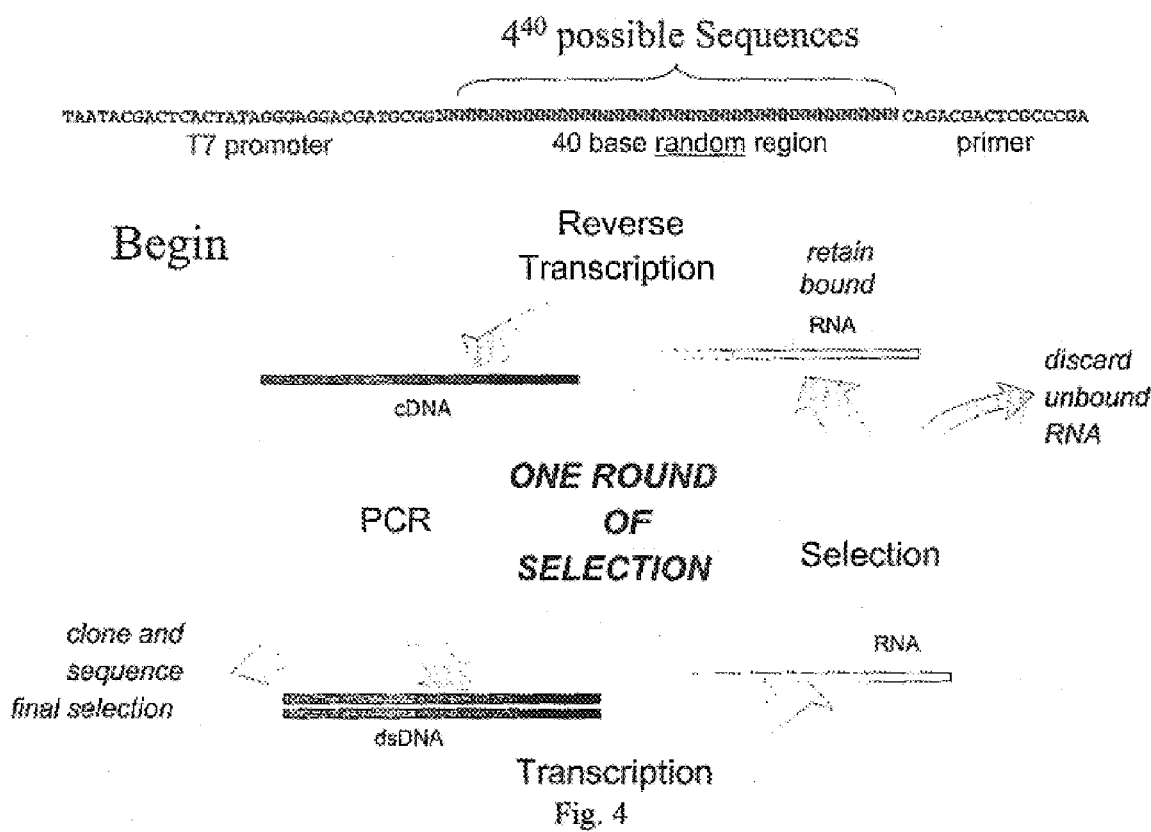
FIG. 4 illustrates schematically in vitro selection as described in Example 1. The applied RNA aptamer library template consists of a 5'-terminal fixed region containing a T7 promoter, an internal random region of 40 consecutive nucleotides, followed by a final fixed primer region. A typical round of selection involves transcription of the RNA library with 2'-fluoro (2'-F) modified pyrimidines, followed by a partitioning step where ligand-bound RNA is separated from non-ligand-bound RNA. The bound RNA is then amplified by RT-PCR and in vitro transcription. Several rounds of in vitro selection are completed until the affinity of the RNA aptamer pool for the target ligand has peaked. The resultant dsDNA is then cloned into a plasmid vector and sequenced. Individual aptamers are then tested for their affinity for the target ligand.

A library of approximately $6 \times 10^{14}$ different nuclease stable RNA molecules was generated by transcription of a random sequence synthetic template. The aptamer library template consisted of a T7 promoter, two terminal fixed regions for PCR amplification, and an internal random region of 40 nucleotides (FIG. 4). Prior to selection, the target protein was bound to magnetic beads, where it retained its enzymatic activity. The random sequence library was incubated with xPSM-magnetic beads and allowed 30 minutes to bind. The protein-bound population was partitioned by magnetic separation, and amplified by reverse transcription and quantitative PCR. The resulting templates were transcribed to generate 2'-F modified RNA for the next cycle of selection.

Six rounds of iterative selection were performed and quantitated as illustrated in Table 1. The stringency of selection was regulated by decreasing the amount of xPSM-magnetic beads available for binding or by decreasing the amount of RNA. The signal to noise ratio peaked at selection round six at 5700 fold, and showed no further improvement up to nine total rounds of selection. The signal/noise ratios depicted in Table 1 were determined by comparison of RNA bound to xPSM beads versus beads alone.

Figure 5:
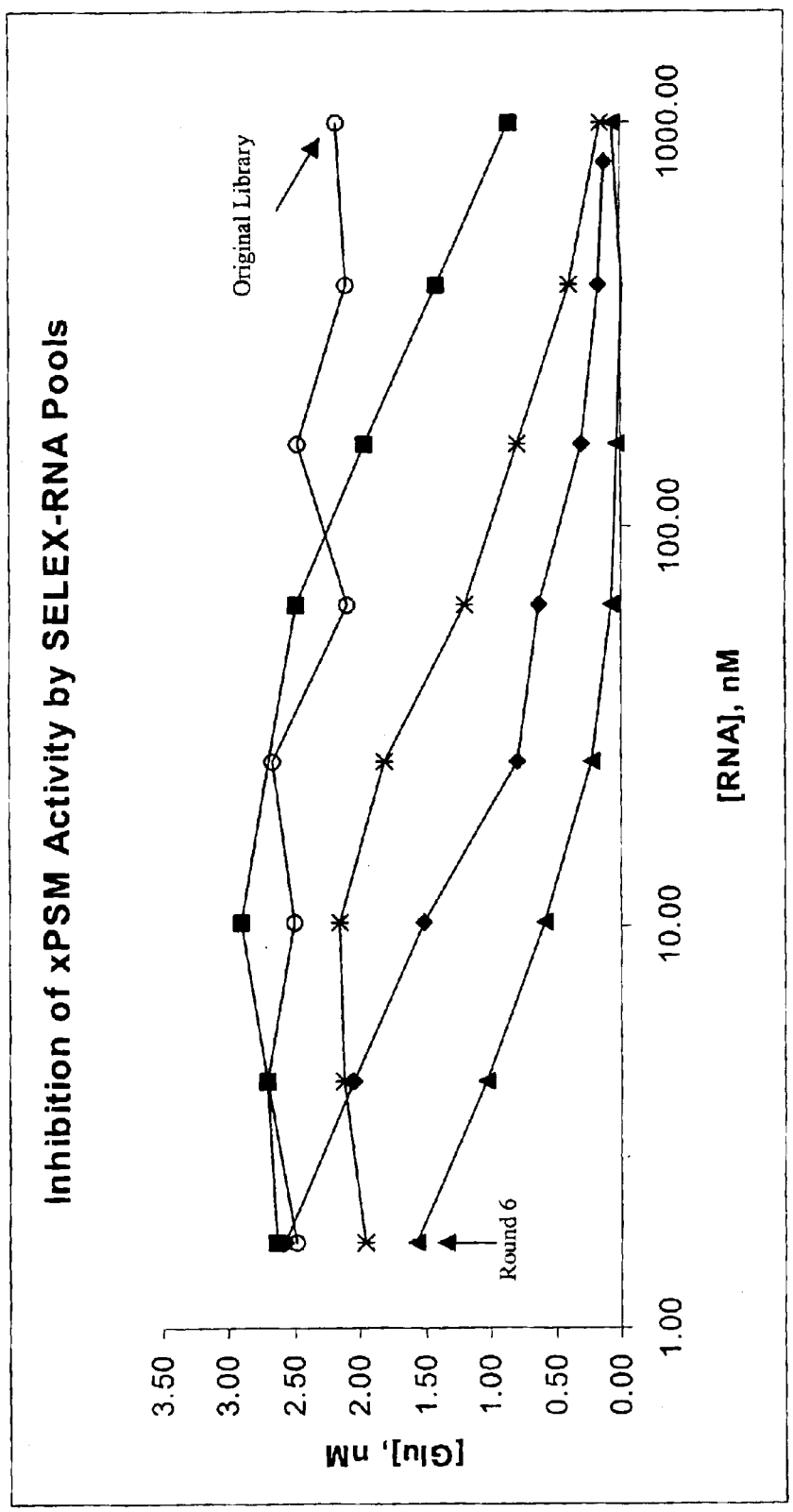
FIG. 5 depicts the inhibition of xPSM activity by SELEX-RNA pools.

Enzyme assays provide a sensitive method to identify and quantitate enzyme ligand interactions. Selected rounds of 2'-F modified RNA were therefore tested for their ability to inhibit xPSM NAALADase activity as described in Example 1. As a control sequence for specificity, the original random sequence library was tested and had no effect on xPSM NAALADase activity, where micromolar aptamer inhibition could be seen as early as round three in selected RNA populations (FIG. 5). The round six RNA aptamer population showed the highest affinity for xPSM, and was therefore used to isolate and sequence individual aptamer clones.

Round six RNA was amplified by RT-PCR and cloned. Sixty randomly picked plasmid clones were sequenced. Ninety-five percent of the sixty clones sequenced were represented by only two sequences. The identified sequences, named xPSM-A9 (SEQ ID NO:5) and xPSM-A10 (SEQ D NO:15) (FIG. 6), are unique, sharing no consensus sequences.

Figure 7A:
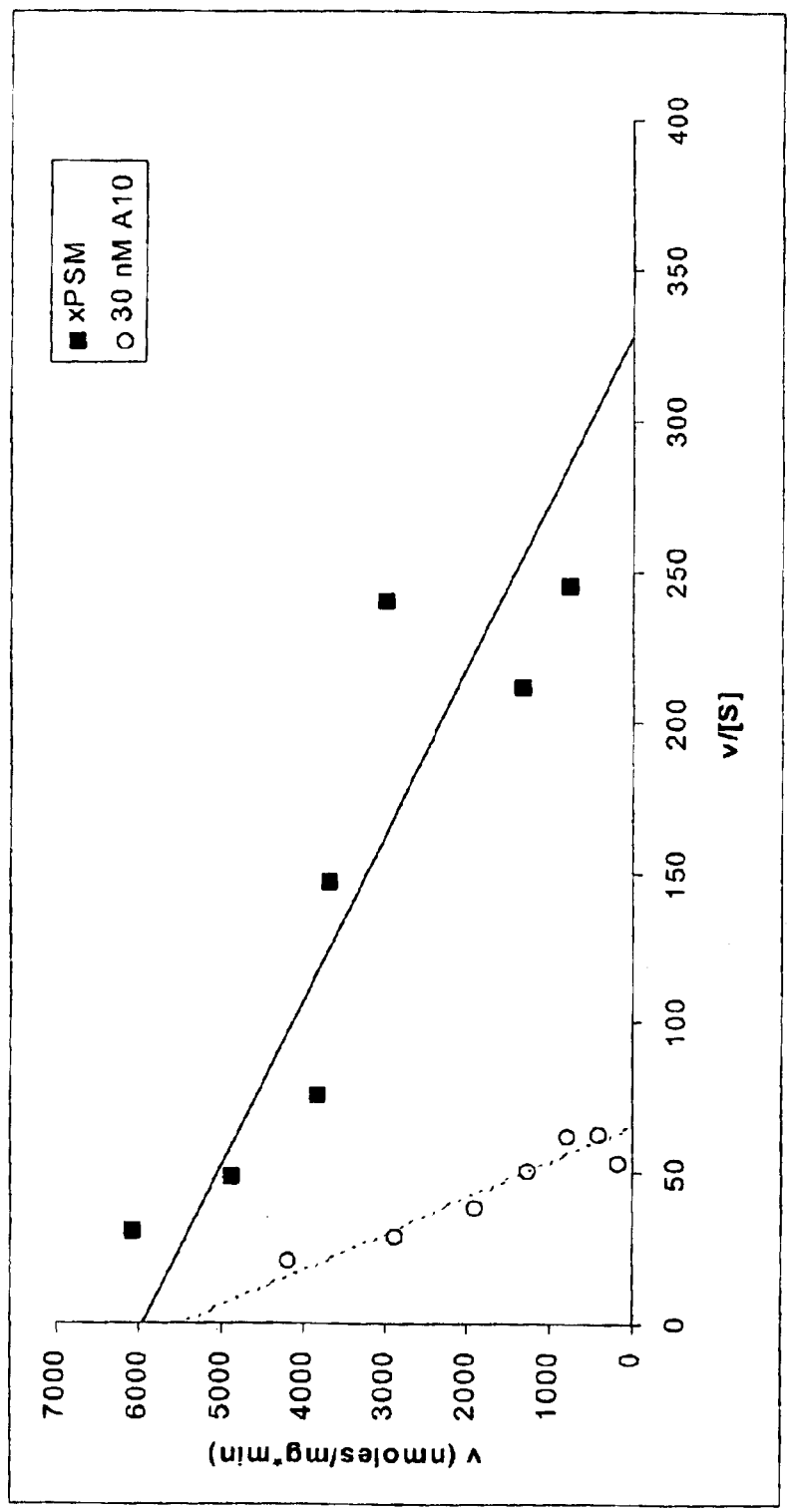
FIGS. 7A and B illustrate graphically that the two aptamers, xPSM-A9 and xPSM-A10 have separate types of inhibition, indicating two separate epitopes.
Figure 7B:
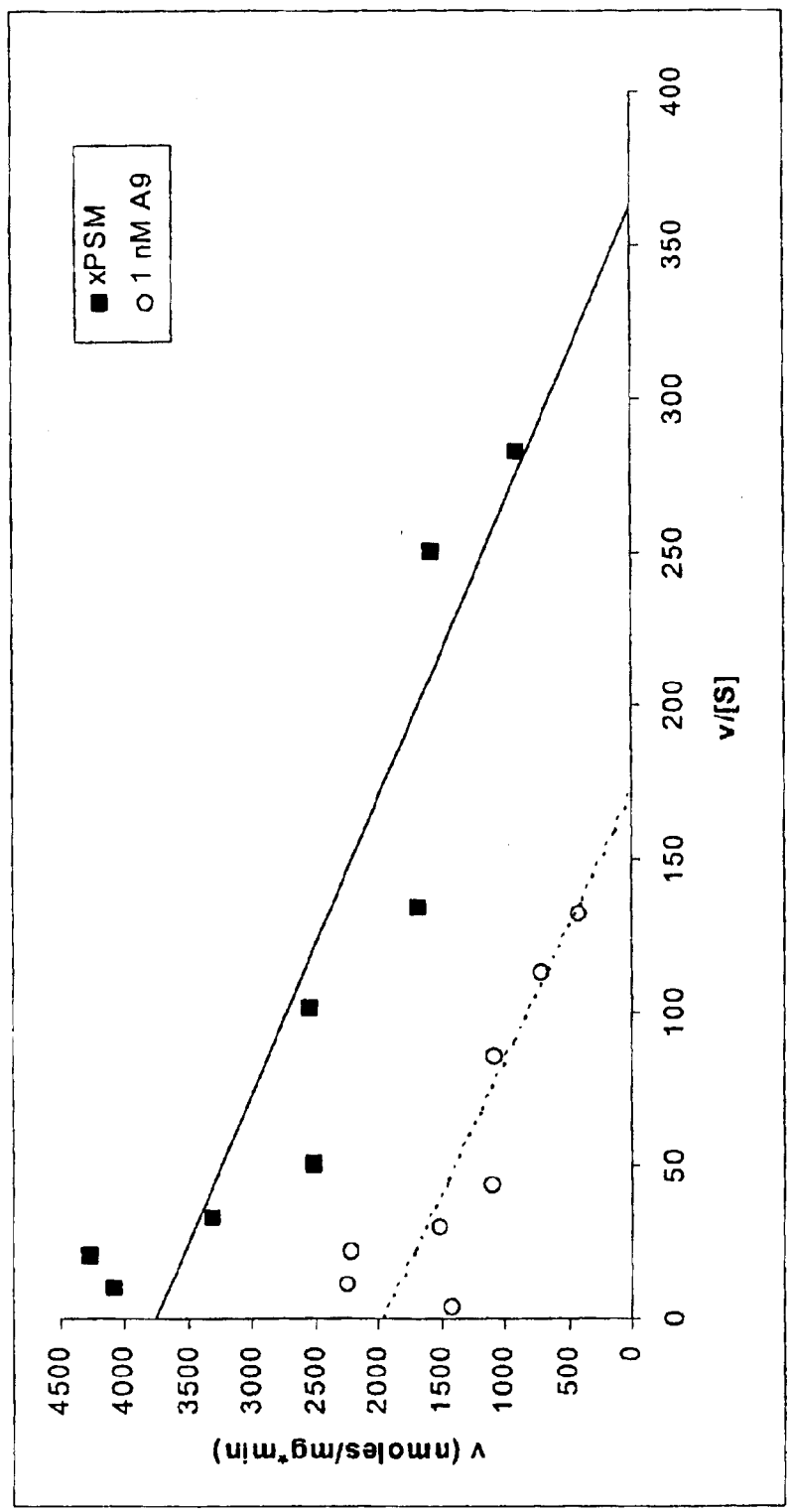

Each aptamer was tested for its affinity based on ability to inhibit NAALADase activity. Aptamer xPSM-A9 displays non-competitive inhibition with a $K_i$ of 1.1 nM (FIG. 7B), whereas aptamer xPSM-A10 shows competitive inhibition with a $K_i$ of 11.9 (FIG. 7A). These two separate modes of inhibition suggest that each aptamer identifies a unique extracellular epitope of PSMA. Both aptamers inhibit native NAALADase activity from LNCaP cells with similar affinity.

Figure 9:
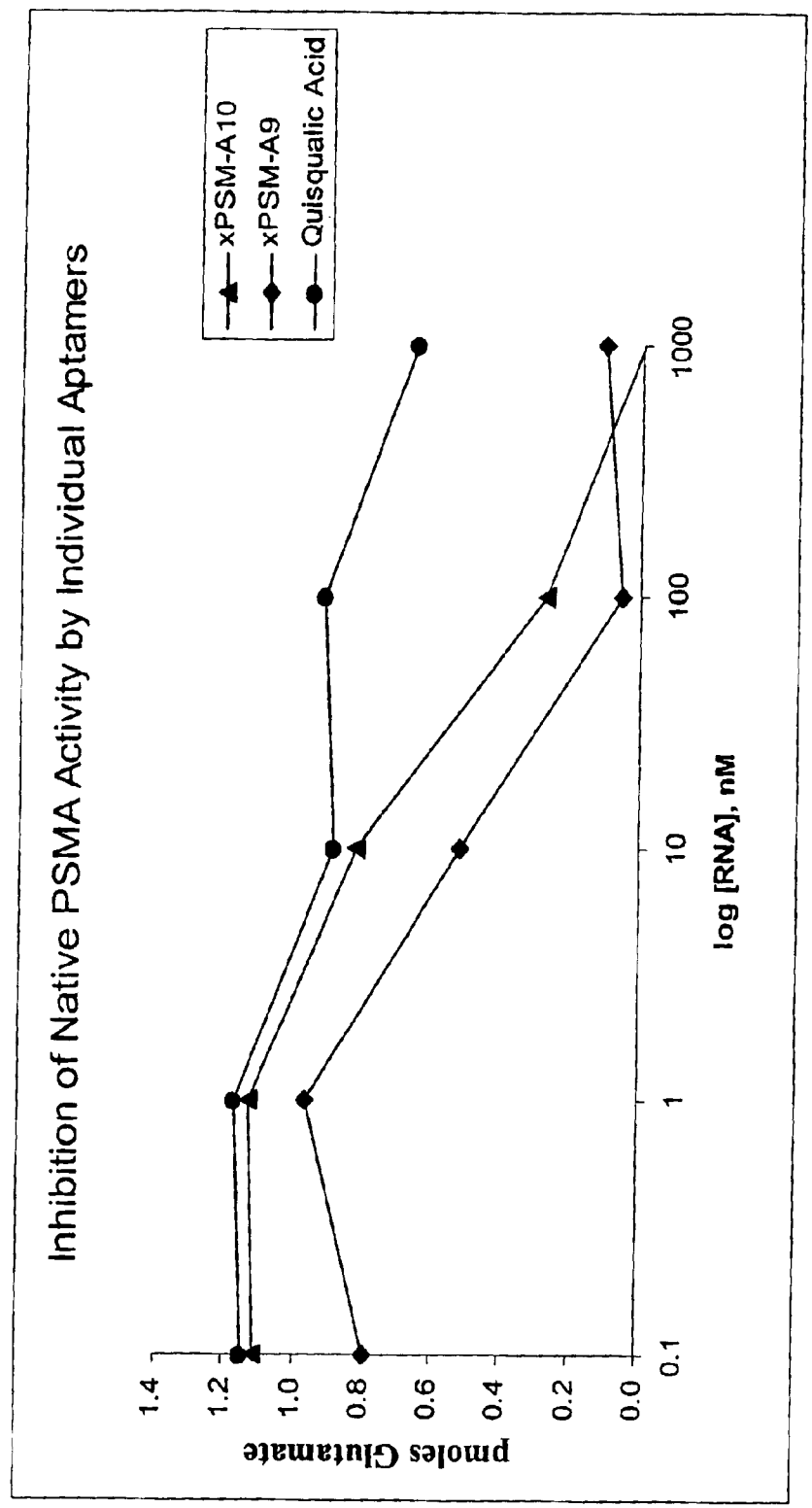
FIG. 9 depicts graphically the NAALADase inhibition of native PSMA by aptamers xPSM-A9 (SEQ ID NO:5) and xPSM-A10 (SEQ ID NO:15).
Figure 10:
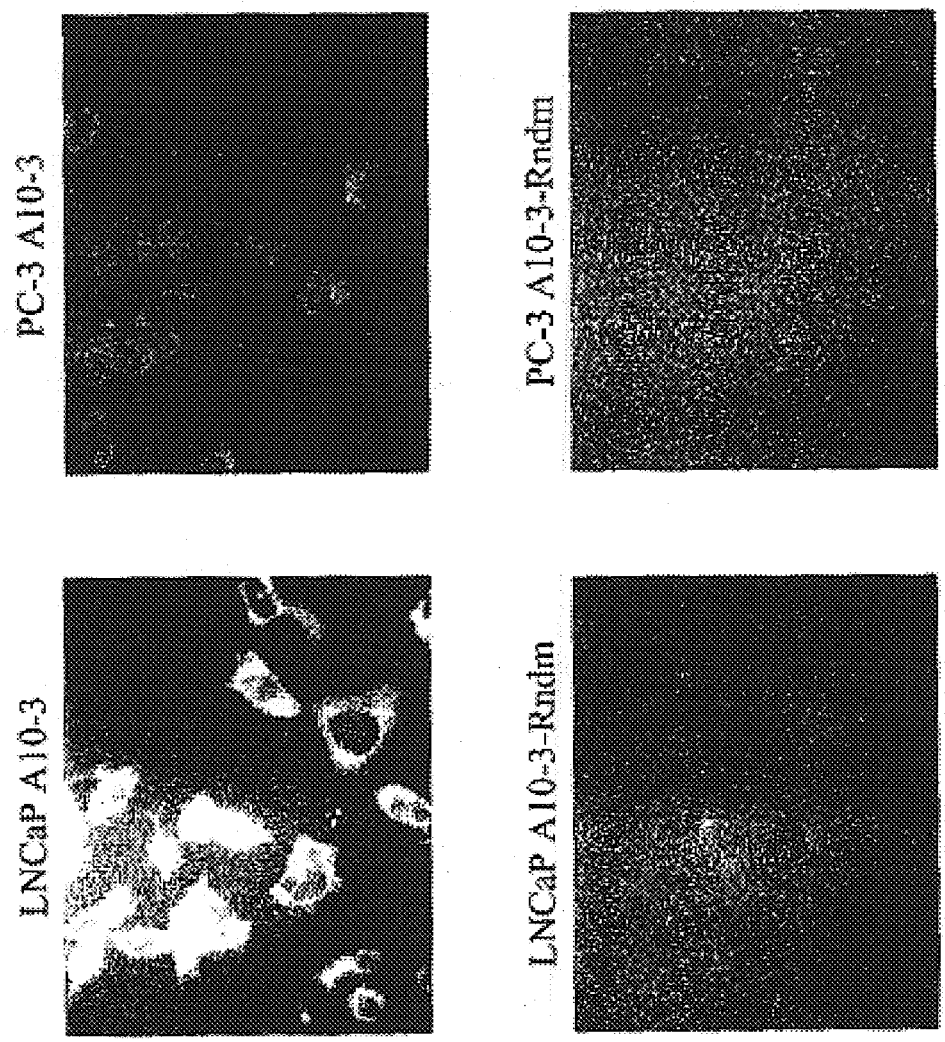
FIG. 10 depicts the ability of aptamer A10-3 to specifically bind native PSMA expressed on the cell surface. Fluorescently labeled A10-3 (50 nM) or A10-3-rndm (A10-3 sequence scrambled) was incubated with formalin fixed LNCaP cells (PSMA positive) and PC-3 cells (PSMA negative) for 12 minutes, washed, and visualized by fluorescent microscopy.

FIGS. 9 and 10 demonstrate aptamer binding native PSMA on the surface of LNCaP cells. This is significant as the data in the previous figures demonstrates aptamer binding the synthetic PSMA, xPSM, purified by baculovirus. The NAALADase assay depicted in FIG. 9 was performed as described in Example 1, except membrane extracts from LNCaP were used instead of purified xPSM. This methodology is described in Carter et al. (1996) Proc Natl Acad Sci USA 93(2):749–53). A known micromolar NAALADase inhibitor, quisqualic acid, is included as a reference control. This demonstrates the potency of the aptamers in comparison to known NAALADase inhibitors.

The smallest aptamer, A10-3, was fluorescently labeled in order to determine if these aptamers could specifically bind cells expressing PSMA. A negative reference control, A10-3-mdm, was developed by randomly scrambling the A10-3 sequence. Binding specificity was demonstrated by fluorescent microscopy where aptamer A10-3 specifically bound PSMA expressing LNCaP cells, but not the negative control PC-3 cells (FIG. 10). As can be seen in FIG. 10 the scrambled A10-3 sequence, A10-3-mdm, shows no specificity for either cell line.

Figure 8:
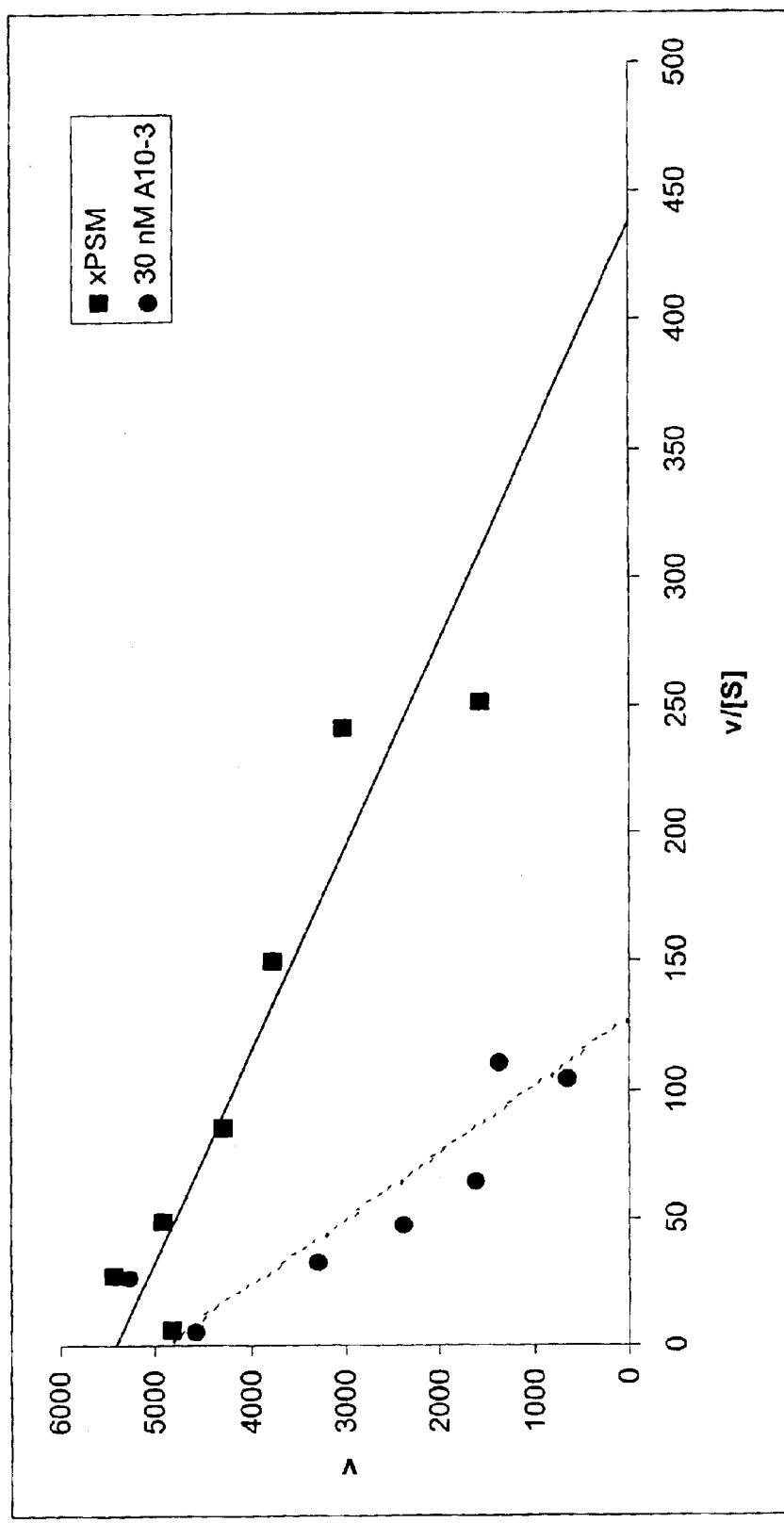
FIG. 8 depicts graphically NAALADase inhibition by the 56-nucleotide xPSM-A10 truncate. Aptamer xPSM-A10-3 (SEQ ID NO:18) is the 15 nucleotide truncate of xPSM-A10. This shorter nucleotide shows competitive inhibition, raising the $K_m$ with no effect on $V_{max}$. Average $K_I$=20.46+/−7.8 nM. $R^2$ values: xPSM 0.8748, xPSM-A10-3 0.7861.

Example 2 describes the determination of minimal size necessary for high affinity binding of two selected nucleic acid ligands to xPSM. Aptamer, xPSM-A10 (SEQ ID NO:15), was successfully truncated to fifty-six nucleotides, or 18.5 kD, while still retaining its ability to inhibit PSMA activity (FIG. 8). These aptamers can be used as inhibitors or be modified to carry agents for imaging or therapeutic treatment.

EXAMPLES

Example 1
Use of SELEX to Obtain Nucleic Acid Ligands to PSMA
Materials and Methods
Cloning PSMA CDNA from LNCaP.

First strand cDNA was synthesized from 2 μg total LNCaP RNA using Superscript II RNase H Reverse Transcriptase (Life Technologies, Inc). Primers homologous to PSMA cDNA bases 134–152 and 2551–2567, flanking the entire full-length PSMA coding region, were used for PCR amplification. Amplification was performed using high fidelity Pfu DNA Polymerase (Stratagene, La Jolla, Calif.). The isolated product was ligated into the pCR-2.1 vector (Invitrogen Corporation, Carlsbad, Calif.). One successful clone, pFULPSM-1, was sequenced and found identical to Genbank accession number M99487. This clone represents the coding region for the full length PSMA protein Preparation of Recombinant PSMA Expressing Baculovirus.

Primers containing restriction enzyme cut sites were designed to overlap the sequence of the entire extracellular portion of PSMA plus a linking glycine, specifically bases 395–422 and 2491–2503. The PCR product was ligated into pBACgus-10 transfer plasmid (Novagen Inc., Madison, Wis.), under the control of the polyhedron promoter. The resulting plasmid, pBACgus-PSM, was sequenced to confirm sequence integrity. Sf-9 cells (ATCC) were co-transfected with pBACgus-PSM and linear high efficiency BacVector-3000 Triple Cut Virus DNA (Novagen Inc) in Grace's Insect Culture Media (Life Technologies, Inc) supplemented with 10% fetal bovine serum. Individual recombinant viral plaques were picked and assayed for recombinant protein expression by S-tag assays and S-tag westerns (Novagen Inc) according to manufacturer's instructions. A single positive clone expressing the entire extracellular portion of PSMA, termed xPSM, was amplified to high titer ($\geq 10^8$ PFU/mL) in 200 mL suspension cultures.

Large Scale xPSM Expression and Purification.

Sf-9 cells (Novagen Inc) were plated as monolayers in Sf-900 II Serum Free Media (Life Technologies Inc) and infected with recombinant virus at an M.O.I of 5. Infected cell media was harvested 72–80 hours post infection and tag-xPSM levels quantitated by S-tag assay (Novagen Inc). Fusion protein was bound by S-protein agarose, washed, and xPSM was released by recombinant enterokinase (rEK) according to manufacturer's instructions (Novagen Inc). Finally, rEK was bound by EKapture Agarose Beads (Novagen Inc) and purified xPSM protein was concentrated by Ultra-Free 15, MWCO 50 kD concentration spin columns (Millipore Co., Bedford, Mass.). xPSM concentrations were determined by Coomassie Plus Protein Assay Reagent (Pierce, Rockford, Ill.). Protein purity was confirmed by silver stain analysis.

Silver Stains. Approximately 100–500 ng of purified PSMA protein was separated by 7.5% SDS-PAGE and stained using the Silver Stain Plus Kit (Bio-Rad Laboratories, Hercules, Calif.). All purified xPSM size and purity was checked by silver stained gels.

PSMA NAALADase Assays.

NAAG hydrolysis was performed essentially as described in Robinson et al. (1987) J Biol Chem. 262:14498–506. LNCaP cell extracts were prepared by sonication in the presence of 50 mM Tris, pH 7.4, 0.5% Triton-X-100. Cell lysate or purified xPSM was incubated in the presence of the radiolabeled substrate N-acetyl-L-aspartyl-L-[3,4-$^3$H] glutamate (NEN Life Science Products, Boston, Mass.) at 37° C. for 10–15 minutes. The reaction was stopped with an equal volume of ice-cold 100 mM sodium phosphate, 2 mM EDTA. Products were separated from intact substrate using anion exchange chromatography and quantitated by scintillation counting. In general, aptamer IC50's were determined in the presence of 8 nM substrate. Aptamer $K_i$'s were determined using 5–30 nM aptamer in serial dilutions of substrate. In all cases less than 20% of substrate was cleaved.

In vitro Selection of PSMA Aptamers.

The SELEX-process has been described in detail in the SELEX Patent Applications. In brief, double-stranded transcription templates were prepared by Klenow fragment extension of 40N7a ssDNA:

5'-TCGCGCGAGTCGTCTG[40N]CCGCATCGTCCT-CCC-3' (SEQ ID NO: 1)

using the 5N7 primer:

5'-TAATACGACTCACTATAGGGAGGACGATG-CGG-3' (SEQ ID NO:2)

which contains the T7 polymerase promoter (underlined). RNA was prepared with T7 RNA polymerase as described previously in Fitzwater and Polisky (1996) Methods Enzymol. 267:275–301, incorporated herein by reference in its entirety. All transcription reactions were performed in the presence of pyrimidine nucleotides that were 2'-fluoro (2'-F) modified on the sugar moiety. This substitution confers enhanced resistance to ribonucleases that utilize the 2'-hydroxyl moiety for cleavage of the phosphodiester bond. Specifically, each transcription mixture contained 3.3 mM 2'-F UTP and 3.3 mM 2'-F CTP along with 1 mM GTP and ATP. The initial randomized RNA library thus produced comprised $6 \times 10^{14}$ molecules (with 1 nmole of RNA).

Nine rounds of the SELEX process were performed as described below, and round six was chosen for cloning based on its ability to inhibit PSMA enzymatic activity.

Target Bead Preparation.

Paramagnetic polystyrene beads were purchased from Dynal, Inc. Dynabeads M-450, uncoated, 4.5 μm, 2.4% w/v. Selections and magnetic separations were performed in a 0.5 mL microfuge tube using a Dynal MPC-E Separator. Prior to use the beads (100 μL) were washed with potassium phosphate (100 mM, 3×500 μL, pH 8.0), 3×500 μL Hepes buffered saline, pH 7.4, MgCl$_2$ (1 mM), CaCl$_2$ (1 mM) (HBSMC). The beads were then resuspend in HBSMC (100 μL) containing 10 μg of the target protein and rotated at 4° C. overnight. The beads were then washed with HBSMC (3×500 μL), resuspended in HBSMC (400 μL) and washed with 3×500 μL HBSMC, HSA (0.01%) and Tween 20 (0.05%) (HBSMCHT). The beads were then resuspended in HBSMCHIT (where "I" refers to I-block) (300 μL, 0.6% solids w/v) and stored at 4° C.

Selection and Partition.

The target beads (50 μL) were pre-blocked for 30 minutes in HBSMCIT at 37° C. The target beads (50 μL) were then combined with the aptamer pool (1 nmole of RNA) in HBSMCHIT (100 μL) buffer and the mixture was rotated for 30 minutes at 37° C. The actual amounts of RNA and beads varied for each round and were decreased in later rounds of selection. The beads were then washed with HBSMCHT (5×500 μL) at 37° C., transferred to a new tube and the final wash (500 μL) was removed.

Elution and Reverse Transcription.

The washed beads were resuspended in 3' primer (20 μL 5 μM), incubated at 95° C. for 5 minutes, and slowly cooled to room temperature. 5× RT master mix (5 ×L) was added and the mixture was incubated at 48° C. for 30 minutes. The reaction mixture was removed from the beads and Quantitative PCR (QPCR) reaction mix was added. Reaction mixtures are summarized in Table 2.

Quantative PCR (QPCR) and Transcription.

cDNA (25 μL) was added to the QPCR master mix (75 μL). Quantitative reference cDNA's and non-template controls were also included for each round. PCR was performed as follows: 35 cycles on QPC machine (ABI 7700) at 95° C. 15 sec, 55° C. 10 sec, 72° C. 30 sec, following an initial 3 minute incubation at 95° C. PCR product (50 μL) was then added to the transcription master mix (150 μL) and the mixture was incubated at 37° C. from 4 to 16 hours, followed by a 10 minute DNAse treatment, and finally gel purification of full length RNA transcript.

Cloning and Sequencing.

Amplified sixth-round oligonucleotide pools were purified on an 8% polyacrylamide gel, reverse transcribed into ssDNA and the DNA amplified by the polymerase chain reaction (PCR) using primers containing BamHI and HindIII restriction endonuclease sites. PCR fragments were cloned, plasmids prepared and sequence analyses performed according to standard techniques (Sambrook et al. (1989) *Molecular Cloning: A Laboratory Manual*, 2$^{nd}$ Ed. 3 vols., Cold Spring Harbor Laboratory Press, Cold Spring Harbor). Plasmids were sequenced using DYEnamic ET-terminator cycle sequencing premix kit (Amersham Pharmacia Biotech, Inc, Piscataway, N.J.) and ABI Prism 377 sequencer.

Fluorescent Staining.

5'-Hexal-amine aptamers A10-3 and A10-3-scrambled (caggcaugccuagcuaagcagcccauggcuuaugcgcggaauauuggc-uuccguuc) 2'FY-aptamers were synthesized with a deoxy-T 3' cap. Aptamers were end labeled with Rhodamine-Red-X succinimidyl ester *5 isomer* (Molecular Probes) according to manufacturer's instructions. Full-length rhodamine-labeled aptamers were gel purified and quantitated. 5×10⁴ LNCaP Parent and PC-3 cells per well were plated on 4 chamber glass slides (Becton Dickinson, Franklin Lakes, N.J.). 24 hours after plating, slides were fixed in 10% buffered formalin for 8–16 hours at room temperature and stored at 4° C. in PBS without magnesium or calcium. Each well was incubated in 50 nM labeled-aptamer in PBS without magnesium or calcium for 10–15 minutes at room temperature. Slides were then rinsed several times in PBS, coverslipped, and sealed. Slides were imaged with a Zeiss Axioskop epifluoresence microscope equipped with a short arc mercury lamp illumination (Carl Zeiss Inc, Thornwood, N.Y.) and cooled CCD camera (Micro MAX Digital Camera, Princeton Instruments, Trenton, N.J.). Images were equally processed in Adobe Photoshop (Adobe Systems Inc., Seattle, Wash.). The results are depicted in FIG. 10.

Example 2

Determination of Minimal Size of Aptamers A10 and A9

To determine minimal aptamer sequences, a series of 3' and 5' truncations were tested for $IC_{50}$. Five nucleotides could be removed from the 3' end of aptamer xPSM-A9 (SEQ ID NO:5) with retention of activity, yielding aptamer A9-1 (SEQ ID NO:6). It was found that at least 15 nucleotides could be deleted from the 3' end of aptamer xPSM-A10 (SEQ ID NO:15) with retention of activity, yielding aptamer A10-3 (SEQ ID NO:18). This 18.5 kD aptamer retains the ability to inhibit xPSM NAALADase activity with a $K_I$ of 20.5 nM. (FIG. 8). The shorter A10-3 could not survive 5'-truncation.

TABLE 1

| Round | Signal/Noise |
|---|---|
| 1 | 3.4 |
| 2 | 26.8 |
| 3 | 15.8 |
| 4 | 25.7 |
| 5 | 125.0 |
| 6 | 5688.0 |

TABLE 2

Reaction mixtures for reverse transcription (RT), QPCR and Transcription

| 5× RT mix | QPCR mix | Transcription mix |
|---|---|---|
| 2.5 μL 10× RT buffer | 10 μL 10× SQ buffer | 40 μL 5× nucleotides |
| 1 μL 25 mM dNTP'S | 1 μL 3' primer 100 μM | 40 μL 5× Ribomax |
| 1 μL H₂O | 0.5 μL 5' primer 100 μM | 10 μL guanosine 100 mM |
| 0.5 μL AMV-RT | 0.5 μL 5' primer-FD2 100 μM | 6 μL T7 RNA Polymerase |
| | 1 μL Taq Polymerase | 2 μL pyro-phosphatase (ppase) |
| | 62 μL H₂O | 52 μL H₂O |

TABLE 3 xPSM-1 Aptamer Sequences.

| | | | $IC_{50}$ | SEQ ID NO: |
|---|---|---|---|---|
| Family #1 | | | | |
| B8 | (31) | GGGAGGACGAUGCGGACCGAAAAAGACCUGACUUCUAUACUAAGUCUACGUACCCAGACGACUCGCCCGA | | 3 |
| A11 | | GGGAGGACGAUGCGGACCGAAAAAGACCUGACUUCUAUACUAAGUCUACGUCCAGACGACUCGCCCGA | | 4 |
| A9 | | GGGAGGACGAUGCGGACCGAAAAAGACCUGACUUCUAUACUAAGUCUACGUUCCCAGACGACUCGCCCGA | 5 nM | 5 |
| xPSM1.A9-1 | | GGGAGGACGAUGCGGACCGAAAAAGACCUGACUUCUAUACUAAGUCUACGUUCCCAGACGACUCG | 8 nM | 6 |
| xPSM1.A9-2 | | GGGAGGACGAUGCGGACCGAAAAAGACCUGACUUCUAUACUAAGUCUACGUUCCCAGACG | 300 nM | 7 |
| xPSM1.A9-3 | | GGGAGGACGAUGCGGACCGAAAAAGACCUGACUUCUAUACUAAGUCUACGUUCCC | >300 nM | 8 |
| xPSM1.A9-3.1 | | GACGAUGCGGACCGAAAAAGACCUGACUUCUAUACUAAGUCUACGUUCCC | | 9 |
| Xpsm1.A9-3.2 | | UGCGGACCGAAAAAGACCUGACUUCUAUACUAAGUCUACGUUCCC | | 10 |
| xPSM1.A9-3.3 | | ACCGAAAAAGACCUGACUUCUAUACUAAGUCUACGUUCCC | | 11 |
| xPSM1.A9-4 | | GGGAGGACGAUGCGGACCGAAAAAGACCUGACUUCUAUACUAAGUCUACG | >300 nM | 12 |
| xPSM1.A9-5 | | GGGAGGACGAUGCGGACCGAAAAAGACCUGACUUCUAUACUAAGU | >300 nM | 13 |
| xPSM1.A9-6 | | GGGAGGACGAUGCGGACCGAAAAAGACCUGACUUCUAUAC | >300 nM | 14 |
| Family #2 | | | | |
| 62-A10 | (20) | GGGAGGACGAUGCGGAUCAGCCAUGUUUACGUCACUCCUUGUCAAUCCUCAUCGGCAGACGACUCGCCCGA | 80 nM | 15 |
| xPSM1.A10-1 | | GGGAGGACGAUGCGGAUCAGCCAUGUUUACGUCACUCCUUGUCAAUCCUCAUCGGCAGACGACUCG | 40 nM | 16 |
| xPSM1.A10-2 | | GGGAGGACGAUGCGGAUCAGCCAUGUUUACGUCACUCCUUGUCAAUCCUCAUCGGCAGACG | | 17 |
| xPSM1.A10-3 | | GGGAGGACGAUGCGGAUCAGCCAUGUUUACGUCACUCCUUGUCAAUCCUCAUCGC | 50 nM | 18 |
| xPSM1.A10-4 | | GGGAGGACGAUGCGGAUCAGCCAUGUUUACGUCACUCCUUGUCAAUCCUCA | >700 nM | 19 |
| xPSM1.A10-5 | | GGGAGGACGAUGCGGAUCAGCCAUGUUUACGUCACUCCUUGUCAAU | >700 nM | 20 |
| xPSM1.A10-6 | | GGGAGGACGAUGCGGAUCAGCCAUGUUUACGUCACUCCUUG | >700 nM | 21 |
| 64-A12 | | GGGAGGACGAUGCGGAUCAGCCAUGUUUACGUCACUCCUUGUCAAUCCUCAUCGCCAGACGACUCGCCCGA | | 22 |
| 11-F9 | | GGGAGGACGAUGCGGAUCAGCCAUGUUUACGUCACUCCUUGGUCAAUCCUCAUCGGCAGACGACUCGCCCGA | | 23 |
| 50-D10 | | GGGAGGACGAUGCGGAUAGCCAUGUUUACGUCACUCCUUGGUCAAUCCUCAUCGCCAGACGACUCGCCCGA | | 24 |
| 22-C8 | | GGGAGGACGAUGCGGAUCAGCCAUGUUUACGUCACUCCUUGACAAUCCUCAUCGGCAGACGACUCGCCCGA | | 25 |
| Others | | | | |
| 27-B3 | | GGGAGGACGATGCGGACGACACGCTCCTCTGATTAG ACTAAAGACCACCGTGCCCAGACGACTCGCCCGA | | 26 |
| 36-H6 | | GGGAGGACGATCGGACCATCGAACAGTGGCTAAAAACCAAGGGCATCATTCGCCCCAGACGACTCGCCCGA | | 27 |

*All pyrimidines are 2'-F, all purines are 2'-OH.
Bases corresponding to 5' and 3' fixed regions are underlined.

What is claimed is:

1. A purified and non-naturally occurring RNA ligand to prostate specific membrane antigen (PSMA) wherein said ligand is selected from the group consisting of SEQ ID NOS:5, 6, 15, 16, 17, and 18.

* * * * *

SEQUENCE LISTING

<160> NUMBER OF SEQ ID NOS: 27

<210> SEQ ID NO 1
<211> LENGTH: 71
<212> TYPE: DNA
<213> ORGANISM: Artificial Sequence
<220> FEATURE:
<223> OTHER INFORMATION: Description of Artificial Sequence: Template
<221> NAME/KEY: misc_feature
<222> LOCATION: (1)..(71)
<223> OTHER INFORMATION: N at positions 17-56 is  A, C, T or G

<400> SEQUENCE: 1
tcgcgcgagt cgtctgnnnn nnnnnnnnnn nnnnnnnnnn nnnnnnnnnn nnnnnnccgc    60
atcgtcctcc c                                                        71

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 2
taatacgact cactataggg aggacgatgc gg                                  32

<210> SEQ ID NO 3
<211> LENGTH: 70
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(70)
<223> OTHER INFORMATION: All pyrimidines are 2'-F and all purines are
      2'-OH

<400> SEQUENCE: 3
gggaggacga ugcggaccga aaaagaccug acuucuauac uaagucuacg uacccagacg    60
acucgcccga                                                          70

<210> SEQ ID NO 4
<211> LENGTH: 70
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(70)
<223> OTHER INFORMATION: All pyrimidines are 2'-F and all purines are
      2'-OH

<400> SEQUENCE: 4
gggaggacga ugcggaccga aaaagaccug acuucuauac uaagucuacg uucucagacg    60
acucgcccga                                                          70

<210> SEQ ID NO 5
<211> LENGTH: 70
<212> TYPE: RNA
<213> ORGANISM: Artificial Sequence
<220> FEATURE:
<223> OTHER INFORMATION: Description of Artificial Sequence: Synthetic
      Nucleic Acid Ligand

```
<221> NAME/KEY: modified_base
<222> LOCATION: (1)..(70)
<223> OTHER INFORMATION: All pyrimidines are 2'-F and all purines are
      2'-OH

<400> SEQUENCE: 5
gggaggacga ugcggaccga aaaagaccug acuucuauac uaagucuacg uucccagacg    60
acucgcccga                                                          70

<210> SEQ ID NO 6
<211> LENGTH: 65
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(65)
<223> OTHER INFORMATION: All pyrimidines are 2'-F and all purines are
      2'-OH

<400> SEQUENCE: 6
gggaggacga ugcggaccga aaaagaccug acuucuauac uaagucuacg uucccagacg    60
acucg                                                               65

<210> SEQ ID NO 7
<211> LENGTH: 60
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(60)
<223> OTHER INFORMATION: All pyrimidines are 2'-F and all purines are
      2'-OH

<400> SEQUENCE: 7
gggaggacga ugcggaccga aaaagaccug acuucuauac uaagucuacg uucccagacg    60

<210> SEQ ID NO 8
<211> LENGTH: 55
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(55)
<223> OTHER INFORMATION: All pyrimidines are 2'-F and all purines are
      2'-OH

<400> SEQUENCE: 8
gggaggacga ugcggaccga aaaagaccug acuucuauac uaagucuacg uuccc         55

<210> SEQ ID NO 9
<211> LENGTH: 50
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(50)
<223> OTHER INFORMATION: All pyrimidines are 2'-F and all purines are
      2'-OH

<400> SEQUENCE: 9
```
gacgaugcgg accgaaaaag accugacuuc uauacuaagu cuacguuccc    50

<210> SEQ ID NO 10
<211> LENGTH: 45
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(45)
<223> OTHER INFORMATION: All pyrimidines are 2'-F and all purines are
      2'-OH

<400> SEQUENCE: 10
ugcggaccga aaagaccug acuucuauac uaagucuacg uuccc    45

<210> SEQ ID NO 11
<211> LENGTH: 40
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(40)
<223> OTHER INFORMATION: All pyrimidines are 2'-F and all purines are
      2'-OH

<400> SEQUENCE: 11
accgaaaaag accugacuuc uauacuaagu cuacguuccc    40

<210> SEQ ID NO 12
<211> LENGTH: 50
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(50)
<223> OTHER INFORMATION: All pyrimidines are 2'-F and all purines are
      2'-OH

<400> SEQUENCE: 12
gggaggacga ugcggaccga aaagaccug acuucuauac uaagucuacg    50

<210> SEQ ID NO 13
<211> LENGTH: 45
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(45)
<223> OTHER INFORMATION: All pyrimidines are 2'-F and all purines are
      2'-OH

<400> SEQUENCE: 13
gggaggacga ugcggaccga aaagaccug acuucuauac uaagu    45

<210> SEQ ID NO 14
<211> LENGTH: 40
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base

```
<222> LOCATION: (1)..(40)
<223> OTHER INFORMATION: All pyrimidines are 2'-F and all purines are
      2'-OH

<400> SEQUENCE: 14
gggaggacga ugcggaccga aaaagaccug acuucuauac                         40

<210> SEQ ID NO 15
<211> LENGTH: 71
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(71)
<223> OTHER INFORMATION: All pyrimidines are 2'-F and all purines are
      2'-OH

<400> SEQUENCE: 15
gggaggacga ugcggaucag ccauguuuac gucacuccuu gucaauccuc aucggcagac   60
gacucgcccg a                                                       71

<210> SEQ ID NO 16
<211> LENGTH: 66
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(66)
<223> OTHER INFORMATION: All pyrimidines are 2'-F and all purines are
      2'-OH

<400> SEQUENCE: 16
gggaggacga ugcggaucag ccauguuuac gucacuccuu gucaauccuc aucggcagac   60
gacucg                                                             66

<210> SEQ ID NO 17
<211> LENGTH: 61
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(61)
<223> OTHER INFORMATION: All pyrimidines are 2'-F and all purines are
      2'-OH

<400> SEQUENCE: 17
gggaggacga ugcggaucag ccauguuuac gucacuccuu gucaauccuc aucggcagac   60
g                                                                  61

<210> SEQ ID NO 18
<211> LENGTH: 56
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(56)
<223> OTHER INFORMATION: All pyrimidines are 2'-F and all purines are
      2'-OH

<400> SEQUENCE: 18
```

```
gggaggacga ugcggaucag ccauguuuac gucacuccuu gucaauccuc aucggc        56
```

<210> SEQ ID NO 19
<211> LENGTH: 51
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(51)
<223> OTHER INFORMATION: All pyrimidines are 2'-F and all purines are
      2'-OH

<400> SEQUENCE: 19

```
gggaggacga ugcggaucag ccauguuuac gucacuccuu gucaauccuc a              51
```

<210> SEQ ID NO 20
<211> LENGTH: 46
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(46)
<223> OTHER INFORMATION: All pyrimidines are 2'-F and all purines are
      2'-OH

<400> SEQUENCE: 20

```
gggaggacga ugcggaucag ccauguuuac gucacuccuu gucaau                    46
```

<210> SEQ ID NO 21
<211> LENGTH: 41
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(41)
<223> OTHER INFORMATION: All pyrimidines are 2'-F and all purines are
      2'-OH

<400> SEQUENCE: 21

```
gggaggacga ugcggaucag ccauguuuac gucacuccuu g                         41
```

<210> SEQ ID NO 22
<211> LENGTH: 71
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(71)
<223> OTHER INFORMATION: All pyrimidines are 2'-F and all purines are
      2'-OH

<400> SEQUENCE: 22

```
gggaggacga ugcggaucag ccauguuuac gucacuccuu gucaauccuc aucgccagac     60
gacucgcccg a                                                          71
```

<210> SEQ ID NO 23
<211> LENGTH: 72
<212> TYPE: RNA
<213> ORGANISM: Artificial Sequence
<220> FEATURE:

```
<223> OTHER INFORMATION: Description of Artificial Sequence: Synthetic
      Nucleic Acid Ligand
<221> NAME/KEY: modified_base
<222> LOCATION: (1)..(72)
<223> OTHER INFORMATION: All pyrimidines are 2'-F and all purines are
      2'-OH

<400> SEQUENCE: 23
gggaggacga ugcggaucag ccauguuuac gucacuccuu ggucaauccu caucggcaga      60
cgacucgccc ga                                                         72

<210> SEQ ID NO 24
<211> LENGTH: 71
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(71)
<223> OTHER INFORMATION: All pyrimidines are 2'-F and all purines are
      2'-OH

<400> SEQUENCE: 24
gggaggacga ugcggauagc cauguuuacg ucacuccuug gucaauccuc aucgccagac      60
gacucgcccg a                                                          71

<210> SEQ ID NO 25
<211> LENGTH: 71
<212> TYPE: RNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(71)
<223> OTHER INFORMATION: All pyrimidines are 2'-F and all purines are
      2'-OH

<400> SEQUENCE: 25
gggaggacga ugcggaucag ccauguuuac gucacuccuu gacaauccuc aucggcagac      60
gacucgcccg a                                                          71

<210> SEQ ID NO 26
<211> LENGTH: 71
<212> TYPE: DNA
<213> ORGANISM: Artificial Sequence
<220> FEATURE:
<223> OTHER INFORMATION: Description of Artificial Sequence: Synthetic
      Nucleic Acid Ligand
<221> NAME/KEY: modified_base
<222> LOCATION: (1)..(71)
<223> OTHER INFORMATION: All pyrimidines are 2'-F and all purines are
      2'-OH
<221> NAME/KEY: misc_feature
<222> LOCATION: (1)..(71)
<223> OTHER INFORMATION: N at position 37 is  A, C, T, G or U

<400> SEQUENCE: 26
gggaggacga tgcggacgac acgctcctct gattagnact aaagaccacc gtgcccagac      60
gactcgcccg a                                                          71

<210> SEQ ID NO 27
<211> LENGTH: 71
<212> TYPE: DNA
<213> ORGANISM: Artificial Sequence
<220> FEATURE:
```

-continued

```
<223> OTHER INFORMATION: Description of Artificial Sequence: Synthetic
      Nucleic Acid Ligand
<221> NAME/KEY: modified_base
<222> LOCATION: (1)..(71)
<223> OTHER INFORMATION: All pyrimidines are 2'-F and all purines are
      2'-OH

<400> SEQUENCE: 27
gggaggacga tcggaccatc gaacagtggc taaaaaccaa gggcatcatt cgccccagac      60
gactcgcccg a                                                          71
```